United States Patent [19]

Yashima et al.

[11] Patent Number: 4,568,769

[45] Date of Patent: Feb. 4, 1986

[54] METHOD FOR PRODUCING A MIXTURE CONTAINING CYCLOALKANONES AND CYCLOALKANOLS

[75] Inventors: Akira Yashima; Teruo Matsuda; Tadao Sato; Mitsuaki Takahashi; Kiyomi Sakai, all of Ehime, Japan

[73] Assignee: Sumitomo Chemical Company, Osaka, Japan

[21] Appl. No.: 622,865

[22] Filed: Jun. 20, 1984

[51] Int. Cl.$^4$ ............................................. C07C 45/53
[52] U.S. Cl. ................................. 568/342; 568/360; 568/836; 568/798
[58] Field of Search ...................... 568/360, 836, 342; 549/198

[56] References Cited

U.S. PATENT DOCUMENTS

| | | | |
|---|---|---|---|
| 3,129,227 | 4/1964 | van Velyen | 548/374 |
| 4,322,562 | 3/1982 | Torrog et al. | 568/360 |
| 4,326,084 | 4/1982 | Druliner | 568/342 |

FOREIGN PATENT DOCUMENTS 115729 9/1981 Japan .................................. 568/342

OTHER PUBLICATIONS

Chem. Abst., vol. 60, #354a (1964).
Kogyo Kagaku Zasshi, vol. 73, pp. 2056 and 2388 (1970) and the corresponding Chemical Abstract, vol. 74, items 75828n and 87175k (1971).

Primary Examiner—James H. Reamer
Attorney, Agent, or Firm—Cushman, Darby & Cushman

[57] ABSTRACT

Disclosed in a method for producing a mixture containing cycloalkanone and/or cycloalkanol which comprises oxidizing a cycloalkane with molecular oxygen to a cycloalkyl hydroperoxide represented by the formula (1):

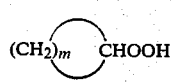

(1)

(wherein m represents an integer of $4 \leq m \leq 11$) and decomposing the cycloalkyl hydroperoxide to obtain a mixture containing cycloalkanone and/or cycloalkanol, wherein the oxidation of the cycloalkane with molecular oxygen and/or the decomposition of the cycloalkyl hydroperoxide are carried out in the presence of a catalyst composition comprising at least one metallic salt represented by the formula (2):

$$MX_n \quad (2)$$

(wherein M represent Co, Mn, Cr or Fe, X represents an anionic ligand and n represents 2 or 3) and at least one compound represented by the formula (3):

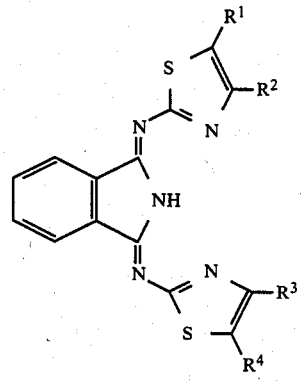

(3)

(wherein $R^1$, $R^2$, $R^3$ and $R^4$ independently represent hydrogen or a lower alkyl group) and/or a catalyst composition comprising at least one metal complex represented by the formula (4):

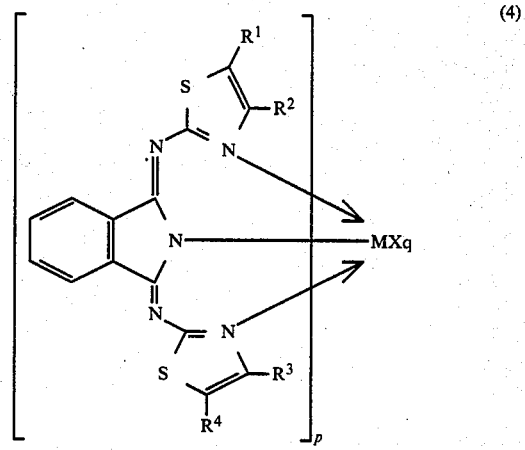

(4)

(wherein M represents Co, Mn, Cr or Fe, X represents an anionic ligand, $R^1$, $R^2$, $R^3$ and $R^4$ independently represent hydrogen or a lower alkyl group, p is 1 or 2 and q is 0, 1 or 2).

Advantages of the method are higher conversion of cycloalkyl hydroperoxide, higher yields of cycloalkanone and cycloalkanol and higher production ratio of cycloalkanone.

12 Claims, No Drawings

METHOD FOR PRODUCING A MIXTURE CONTAINING CYCLOALKANONES AND CYCLOALKANOLS

BACKGROUND OF THE INVENTION

This invention relates to a method for producing a mixture containing cycloalkanones and/or cycloalkanols which comprises oxidizing a cycloalkane with molecular oxygen to a cycloalkyl hydroperoxide and decomposing the cycloalkyl hydroperoxide.

The oxidation reaction of a cycloalkane with molecular oxygen generally belongs to an autoxidation reaction and comprises the stage where a cycloalkyl hydroperoxide is produced from a cycloalkane and molecular oxygen and the stage where said cycloalkyl hydroperoxide decomposes to produce a cycloalkane and a cycloalkanol. The reaction of the first stage proceeds with relatively high yields while in the reaction of the second stage the decomposition degree of the cycloalkyl hydroperoxide differs greatly depending on the catalysts present in the system.

Hitherto, decomposition of cycloalkyl hydroperoxides has been effected in the presence of metallic salts. For example, "Kogyo Kagaku Zasshi" 73, 2056 (1970) reports the decomposition of cyclohexyl hydroperoxide with cobalt oxide, but this is not necessarily satisfactory because catalysts in high concentrations of several thousands ppm must be used to obtain sufficiently high decomposition rates.

Furthermore, "Kogyo Kagaku Zasshi", 73, 2388 (1970) reports the decomposition of cyclohexyl hydroperoxide with cobalt naphthenate, etc. However, this requires the high decomposition temperature of 160° C. in spite of using a high catalyst concentration of 10 ppm.

U.S. application No. 187719 discloses the decomposition of cyclohexyl hydroperoxide with bis(pyridylimino)isoindoline complexes of cobalt and the like. However, according to this method the ratio of the resultant cyclohexanone and cyclohexanol is small, namely, about 0.2 and selectivity to cyclohexanone is low. Industrially, the mixtures of cyclohexanone and cyclohexanol are used mainly as starting materials for ε-caprolactam and adipic acid. Production of ε-caprolactam requires cyclohexanone and thus the step of dehydrogenation of cyclohexanol to cyclohexanone is necessary. Therefore, the higher production ratio of cyclohexanone is desired. When the mixture is used for production of adipic acid, the yield of adipic acid is maximum in the case of the ratio of cyclohexanone and cyclohexanol being 0.67 according to U.S. Pat. No. 3,987,100. Thus, the higher production ratio of cyclohexanone is desired. That is, the higher production ratio is desired in decomposition of cyclohexyl hydroperoxide.

The inventors have made intensive researches on the method for producing a cycloalkanone and a cycloalkanol by decomposing a cycloalkyl hydroperoxide where decomposition rate of cycloalkyl hydroperoxide is high, yields of cycloalkanone and cycloalkanol are high, and the production ratio of cycloalkanone is high, and as a result this invention has been attained.

SUMMARY OF THE INVENTION

That is, this invention relates to a method for producing a mixture containing cycloalkanone and/or cycloalkanol which comprises oxidizing a cycloalkane with molecular oxygen to a cycloalkyl hydroperoxide represented by the formula (1):

(1)

(wherein m represents an integer of $4 \leq m \leq 11$) and decomposing the cycloalkyl hydroperoxide to obtain a mixture containing cycloalkanone and/or cycloalkanol, characterized in that the oxidation of the cycloalkane with molecular oxygen and/or the decomposition of the cycloalkyl hydroperoxide are carried out in the presence of a catalyst composition comprising at least one metallic salt represented by the formula (2):

$$MX_n \quad (2)$$

(wherein M represents Co, Mn, Cr or Fe, X represents an anionic ligand and n represents 2 or 3) and at least one compound repesented by the formula (3):

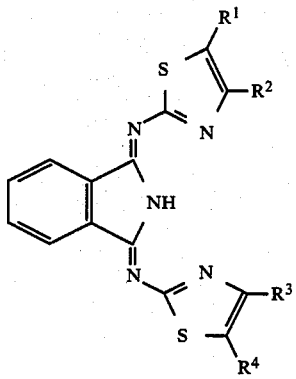

(3)

(wherein $R^1$, $R^2$, $R^3$ and $R^4$ independently represent hydrogen or a lower alkyl group) and/or a catalyst composition comprising at least one metal complex represented by the formula (4):

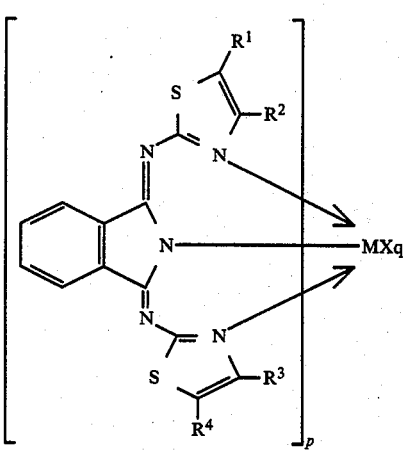

(4)

(wherein M represents Co, Mn, Cr or Fe, X represents an anionic ligand, $R^1$, $R^2$, $R^3$ and $R^4$ independently represent hydrogen or a lower alkyl group, p is 1 or 2 and q is 0, 1 or 2).

Advantages of the method of this invention over the conventional methods are, for example, that higher conversion of cycloalkyl hydroperoxide is attained than with cobalt naphthenate and higher yields of cycloalkanone and cycloalkanol are obtained than with cobalt naphthenate and that higher production ratio of cycloalkanone is obtained than with bis(-pyridylimino)isoindoline complex of cobalt.

DESCRIPTION OF THE PREFERRED EMBODIMENTS

The cycloalkanes used in this invention are those which contain 5 to 12 carbon atoms such as cyclopentane, cyclohexane, cyclooctane, cyclododecane, etc. Industrially, cyclohexane is especially preferred.

The cycloalkyl hydroperoxides (1) are those which are obtained by oxidation of cycloalkanes with molecular oxygen. As examples of them, mention may be made of cyclopentyl hydroperoxide, cyclohexyl hydroperoxide, cyclooctyl hydroperoxide, cyclododecyl hydroperoxide, etc. in correspondence to the above exemplified cycloalkanes.

With reference to the metallic compounds (2), the metal M is Co, Mn, Cr or Fe, and preferably Co.

The anionic ligands X are selected from organic acid groups, inorganic acid groups, hydroxyl groups and oxygen. Examples of the organic acids are carboxylic acids, organic sulfonic acids, organic phosphoric acids, etc. Examples of the carboxylic acids are acetic acid, propionic acid, 2-ethylhexanoic acid, octylic acid, naphthenic acids, etc. Examples of the organic sulfonic acids are p-toluenesulfonic acid, dodecylbenzenesulfonic acid, etc. Examples of the organic phosphoric acids are monotridecylphosphoric acid, etc. Examples of the inorganic acids are sulfuric acid, nitric acid, etc.

As examples of the metallic compounds (2), mention may be made of Co salts, Mn salts, Cr salts and Fe salts of acetic acid, 2-ethylhexanoic acid, naphthenic acid, p-toluenesulfonic acid, monotridecylphosphoric acid and sulfuric acid, hydroxides of Co, Mn, Cr and Fe and oxides of Co, Mn, Cr and Fe. Preferred are Co salts of carboxylic acids, especially preferred are cobalt 2-ethylhexanoate, cobalt octylate and cobalt naphthenate.

Isoindolines (3) include 1,3-bis(2-thiazolylimino)isoindoline (abbreviated as "BTIH" hereinafter) and derivatives thereof.

The lower alkyl groups of the isoindolines mean alkyl groups of 1 to 6 carbon atoms such as methyl, ethyl, hexyl, t-butyl, etc.

Examples of the isoindolines (3) are 1,3-bis(2-thiazolylimino)isoindoline, 1,3-bis(4-methyl-2-thiazolylimino)isoindoline (abbreviated as "4MeBTIH" hereinafter), 1,3-bis(5-methyl-2-thiazolylimino)isoindoline (abbreviated as "5MeBTIH" hereinafter), etc.

As mentioned above,, the catalyst composition used in the method of this invention is a mixture of the metallic compound (2) and the isoindoline (3), but may also be the metal complex (4).

In the metal complexes (4), M, X, $R^1$, $R^2$, $R^3$ and $R^4$ are as mentioned hereinabove and examples thereof are $Co(BTI)_2$, $Co(4MeBTI)_2$, $Co(5MeBTI)_2$, $Co(BTI)OCOCH_3$, etc. which are cobalt derivatives of BTIH.

It can be presumed that the mixtures of the metallic salt compound (2) and the isoindoline (3) produce compounds similar to the metal complexes (4) in the reaction systems and thus the two catalyst compositions can be said to be essentially identical.

This invention can be applied to both the cases where oxidation of cycloalkanes and decomposition of cycloalkyl hydroperoxides are separately carried out and simultaneously carried out.

Decomposition of cycloalkyl hydroperoxides is usually effected in solutions in suitable solvents. Suitable solvents are alkanes such as hexane and octane, cycloalkanes such as cyclopentane and cyclohexane, aromatic hydrocarbons such as benzene, etc. Especially preferred are cycloalkanes corresponding to the cycloalkyl hydroperoxides.

These solutions may be those of isolated cycloalkyl hydroperoxides dissolved in the solvents, but cycloalkane oxidation reaction mixtures per se or those which are diluted or concentrated to a suitable concentration are preferred.

Concentration of the cycloalkyl hydroperoxides used in the method of this invention is 0.1 to 10% by weight, preferably 0.5 to 5% by weight.

Amount of the metallic compounds (2) (in terms of metal) used in the method of this invention is 0.1 to 100 ppm, preferably 0.3 to 5 ppm of the entire mixture. When less than 0.1 ppm, sufficient effect cannot be exhibited and when more than 100 ppm, the effects are no longer increased.

Amount of the isoindolines (3) is 0.1 to 100, preferably 1 to 10 in molar ratio to the metallic compound (2). When less than 0.1, the effects are small and when more than 100, the effects are no longer increased.

The metallic compound (2) and the isoindoline (3) may be added separately to the reaction mixture or they may be added as a mixture.

When the metal complex (4) is used, amount thereof (in terms of metal) is 0.1 to 100 ppm, preferably 0.3 to 5 ppm of the entire compound. When less than 0.1 ppm, the effects are small and when more than 100 ppm, no further increase of the effects can be expected.

The metallic compounds (2), the isoindolines (3) and the metal complex (4) used in the method of this invention may be added as they are, but they may also be added as solutions in solvents such as hydrocarbons, alcohols, ketones, etc.

The method of this invention may be carried out in the presence or absence of molecular oxygen. When molecular oxygen is present, yields of products cycloalkanones and cycloalkanols can be increased without disturbing the decomposition of cycloalkyl hydroperoxide. Thus, presence of molecular oxygen is preferred.

Oxygen is generally used as mixtures with inert gases such as argon and nitrogen. Examples of such mixtures are air, oxygen-added air and nitrogen-added air and air without any pretreatment may be advantageously used.

Reaction temperature employed in the method of this invention may be 80° to 200° C., especially preferably 100° to 160° C. Reaction time is 1 to 120 minutes and reaction pressure is 2 to 20 kg/cm²G.

This invention will be further explained in the following Examples.

In these Examples, conversion, selectivity and production ratio were calculated by the following formulas.

$$\text{Conversion (\%)} = \frac{\text{Consumed cyclohexyl hydroperoxide}}{\text{Charged cyclohexyl hydroperoxide}} \times 100$$

$$\text{Selectivity (\%)} = \frac{\text{Produced cyclohexanone} + \text{Produced cyclohexanol}}{\text{Consumed cyclohexyl hydroperoxide}} \times 100$$

$$\text{Production ratio of cyclohexanone and cyclohexanol} = \frac{\text{Produced cyclohexanone}}{\text{Produced cyclohexanol}}$$

EXAMPLE 1

In a glass autoclave were charged 0.5 part by weight of cyclohexyl hydroperoxide, 50 parts by weight of cyclohexane, 0.00005 part by weight (in terms of cobalt) of cobalt naphthenate and 0.0003 part by weight of BTIH. Then, gas phase part in the autoclave was replaced with nitrogen and thereafter decomposition reaction was carried out while stirring at 140° C. for 20 minutes. After completion of the reaction the reaction mixture was taken out from the autoclave and this reaction mixture was analyzed by gas chromatography and iodometry. The results were as follows: conversion of cyclohexyl hydroperoxide 99%; selectivity to cyclohexanone and cyclohexanol 130%; and production ratio of cyclohexanone and cyclohexanol 0.34.

COMPARATIVE EXAMPLE 1

Example 1 was repeated except that BTIH was not added. The results were as follows: conversion of cyclohexyl hydroperoxide 40%; selectivity to cyclohexanone and cyclohexanol 115%; and production ratio of cyclohexanone and cyclohexanol 0.50.

COMPARATIVE EXAMPLE 2

Example 1 was repeated except that 0.0003 part by weight of 1,3-bis(2-pyridylimino)isoindoline was used in place of BTIH. The results were as follows: conversion of cyclohexyl hydroperoxide 99%; selectivity to cyclohexanone and cyclohexanol 128%; and production ratio of cyclohexanone and cyclohexanol 0.23.

EXAMPLE 2

In a glass autoclave of 500 ml internal volume were charged 0.0004 part by weight of $Co(BTI)OCOCH_3$ and 50 parts by weight of a mixture containing 0.5 part by weight of cyclohexyl hydroperoxide and totally 2 parts by weight of cyclohexanone and cyclohexanol, said mixture being obtained by liquid phase oxidation of cyclohexanone with air. Then, the autoclave was closed keeping air atmosphere in the gas phase part of the autoclave and subsequently decomposition reaction was carried out while stirring at 140° C. for 60 minutes. After the reaction, the reaction mixture was taken out from the autoclave and analyzed in the same manner as in Example 1. The results were as follows: conversion of cyclohexyl hydroperoxide 99%; and selectivity to cyclohexanone and cyclohexanol 220%.

We claim:

1. A method for producing a mixture containing cycloalkanone and/or cycloalkanol which comprises oxidizing a cycloalkane with molecular oxygen to a cycloalkyl hydroperoxide represented by the formula (1):

 (1)

(wherein m represents an integer of $4 \leq m \leq 11$) and decomposing the resultant cycloalkyl hydroperoxide to produce a mixture containing cycloalkanone and/or cycloalkanol wherein the improvement comprises carrying out the oxidation of the cycloalkane with molecular oxygen and/or the decomposition of the cycloalkyl hydroperoxide in the presence of a catalyst composition comprising at least one metallic compound represented by the formula (2):

$$MX_n \qquad (2)$$

(wherein M represents Co, Mn, Cr or Fe, X represents an anionic ligand and n represents 2 or 3) and at least one isoindoline represented by the formula (3):

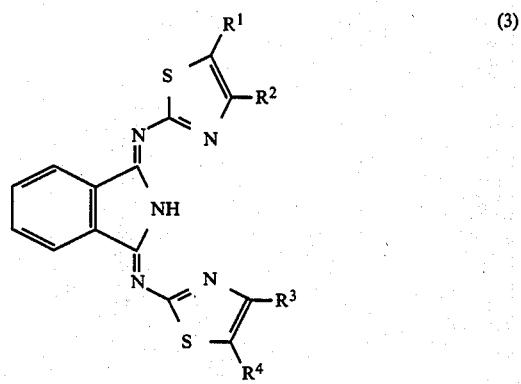 (3)

(wherein $R^1$, $R^2$, $R^3$ and $R^4$ independently represent hydrogen or a lower alkyl group) and/or a catalyst composition comprising at least one metal complex represented by the formula (4):

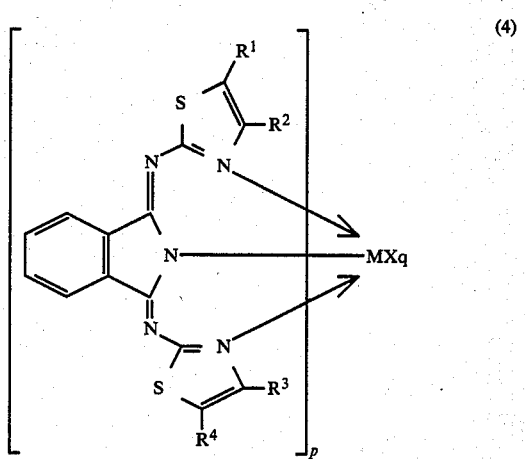 (4)

(wherein M represents Co, Mn, Cr or Fe, X represents an anionic ligand, $R^1$, $R^2$, $R^3$ and $R^4$ independently represent hydrogen or a lower alkyl group, p represents 1 or 2 and q represents 0, 1 or 2).

2. The method according to claim 1 wherein the cycloalkane to be oxidized with molecular oxygen has 5 to 12 carbon atoms.

3. The method according to claim 1 wherein the metal M in the metallic compound (2) and the metal complex (4) is Co.

4. The method according to claim 1 wherein the anionic ligand X in the metallic compound (2) and the metal complex (4) is selected from organic acid group, inorganic acid group and oxygen.

5. The method according to claim 1 wherein the lower alkyl group in the isoindolines (3) and the metal complex (4) has 1 to 6 carbon atoms.

6. The method according to claim 1 wherein the concentration of the cycloalkyl hydroperoxide is 0.1 to 10% by weight.

7. The method according to claim 1 wherein the amount of the metallic compound (2) in terms of metal is 0.1 to 100 ppm of the entire mixture.

8. The method according to claim 1 wherein the amount of the isoindoline (3) is 0.1 to 100 in molar ratio to the metallic compound (2).

9. The method according to claim 1 wherein the amount of the metal complex (4) in terms of metal is 0.1 to 100 ppm of the entire compound.

10. The method according to claim 1 wherein the reaction temperature is 80° to 200° C.

11. The method according to claim 1 wherein the reaction time is 1 to 120 minutes.

12. The method according to claim 1 wherein the reaction pressure is 2 to 20 kg/cm$^2$G.

* * * * *